United States Patent [19]

Schwartz

[11] Patent Number: 4,567,148
[45] Date of Patent: Jan. 28, 1986

[54] METHOD FOR QUANTITATIVELY DETERMINING THE AMOUNT OF HEMOGLOBIN IN A BIOLOGICAL SAMPLE

[75] Inventor: Samuel Schwartz, St. Louis Park, Minn.

[73] Assignee: Regents of the University of Minnesota, Minneapolis, Minn.

[21] Appl. No.: 418,282

[22] Filed: Sep. 13, 1982

Related U.S. Application Data

[63] Continuation-in-part of Ser. No. 190,399, Sep. 24, 1980, Pat. No. 4,378,971.

[51] Int. Cl.⁴ ............................................. G01N 33/72
[52] U.S. Cl. ........................................ 436/66; 436/97; 436/172; 436/178
[58] Field of Search ................... 436/66, 97, 178, 172, 436/174

[56] References Cited

U.S. PATENT DOCUMENTS 3,874,853  4/1975  Byrnes ................................. 436/105
4,035,150  7/1977  Jaffe .................................... 436/66
4,378,971  4/1983  Schwartz ............................ 436/66

OTHER PUBLICATIONS

Henry et al., Clinical Chemistry-Principles and Techniques, 2nd Edition, Harper & Row, New York, 1974, pp. 1215-1263.
Morrison, Analytical Chemistry, vol. 37, No. 9, Aug. 1965, pp. 1124-1126.

Primary Examiner—Arnold Turk
Attorney, Agent, or Firm—Dorsey & Whitney

[57] ABSTRACT

A method of quantitatively determining the amount of hemoglobin in a biological material which includes the steps of preparing a test sample of the biological material by removing contaminating elements such as sources of interfering fluorescence, converting the hemoglobin in the test sample to porphyrin, performing an extraction step for the purpose of separating the porphyrins derived from hemoglobin from various contaminants and determining the level of porphyrin in the test sample by means such as fluorescence assay.

22 Claims, 1 Drawing Figure

METHOD FOR QUANTITATIVELY DETERMINING THE AMOUNT OF HEMOGLOBIN IN A BIOLOGICAL SAMPLE

This is a continuation-in-part of Application Ser. No. 190,399, filed Sept. 24, 1980, U.S. Pat. No. 4,378,971.

BACKGROUND OF THE INVENTION

The present invention relates generally to a method for determining the amount of hemoglobin in a biological sample such as feces, urine or gastric juice, and more particularly, to a quantitative method of determining the amount of such hemoglobin including converting the hemoglobin to porphyrin, isolating and separating out these porphyrins derived from hemoglobin or heme related compounds and determining the level of such porphyrins. This determination is preferably accomplished by means such as a fluorescence assay.

Various rapid screening tests for determining the presence of increased amounts of hemoglobin in biological materials such as feces, urine and gastric juice and currently available. These tests are used throughout the medical profession as a primary screening test for intestinal tumors. Some of these tests which are applicable primarily for feces are indirect tests based upon the peroxidase-like (pseudoperoxidase) activity of the hemoglobin. In these tests, colorless leuco dyes, in the presence of hemoglobin, become colored following addition of a suitable peroxide. These tests do not yield quantitative data and contain a relatively high percentage of false positive and false negative results. My prior patent application Ser. No. 190,399, filed Sept. 24, 1980, U.S. Pat. No. 4,378,971 describes an improved method for determining the level of hemoglobin in a biological sample such as feces, urine or gastric juice. This improved method enables the quantitative determination of hemoglobin in such sample by utilizing a concept of collecting and preparing the test sample, converting the non-fluorescing heme portion of the hemoglobin in the sample to fluorescing porphyrin and then assaying the fluorescence of the converted porphyrins. While this general approach and method are a significant improvement over the prior rapid screening non-quantitative techniques, and thus are highly satisfactory and acceptable in many cases, there is still room for further improvement in the accuracy of the quantitative determination.

One limitation of quantitative tests based upon a determination of converted porphyrins, such as the method described in my copending application referenced above, arises as a result of the existence of impurities in the test sample. These impurities alter the porphyrin determination, thus in turn affecting the accuracy of the hemoglobin determination. This is particularly true where the porphyrin determination is accomplished via a fluorescence assay. For example, biological materials such as feces contain many compounds which fluoresce at wavelengths similar to those of porphyrins derived from hemoglobin. These potential contaminants include naturally occurring porphyrins such as coproporphyrin which are not derived from hemoglobin and ingested prophyrins such as chlorophyll. These potential contaminants can also include numerous other compounds including various pigments and medicines whose fluorescence coincides with the region of maximum porphyrin fluorescence. The fluorescence of contaminants such as these normally exceeds that which is derived from the converted hemoglobin, and thus significantly affects the fluorescence assay in a test of the type described above.

Accordingly, there is a need for a procedure to purify and isolate the porphyrins derived from hemoglobin in a quantitative test for hemoglobin employing a porphyrin determination.

SUMMARY OF THE INVENTION

The method of the present invention overcomes the limitations in quantitative hemoglobin tests which employ a porphyrin determination by isolating and separating out the porphyrins derived from conversion of hemoglobin to porphyrin. This method generally includes an extraction procedure which allows removal from the test sample of significant contaminating elements such as sources of interfering fluorescence. Following this extraction procedure, the sample includes only those porphyrins derived from hemoglobin and related heme compounds. Thus, by assaying the fluorescence of these porphyrins, an accurate quantitative measure of the hemoglobin in the biological sample can be determined. Results have shown that following this procedure, over 90 percent of the fluorescence assayed is due to protoporphyrin and other porphyrins derived from heme compounds.

While the extraction procedure of the present invention enables one to isolate the porphyrins in the biological sample derived from hemoglobin, and thus enables one to assay the fluorescence and accurately determine the amount of hemoglobin in the sample, further benefits can be achieved, particularly with feces, by also performing the extraction procedure on a second test sample in which there is no externally stimulated chemical conversion of hemoglobin to porphyrin. It has been found that a variable, and often major, portion of the hemoglobin pigment which enters the gastrointestinal tract is converted to porphyrins by certain intestinal bacteria. These bacteria and their precise products have not been well defined. They are presumed to be so-called "anaerobes", which are believed to be present in the gastrointestinal tract, especially in the large bowel. The porphyrins which are formed from hemoglobin heme by these bacteria become part of the porphyrins to be determined. If the porphyrin determination in accordance with the procedure of the present invention is made with no externally stimulated conversion, the amount of hemoglobin converted only by bacteria can be determined. By comparing the data from this second test sample in which the hemoglobin converted only by bacteria is determined with the data from the first test sample in which the total hemoglobin is determined, significant information may be obtained as to the location of the source of bleeding. For example, a relatively low proportion of readings of hemoglobin converted only by intestinal bacteria compared to readings for total hemoglobin (on the order of less than 10 percent) would indicate bleeding relatively low in the gastrointestinal tract. On the other hand, a relatively high proportion (on the order of more than 30 or 40 percent) would indicate bleeding in a upper portion of the gastrointestinal tract. It has been shown that in many cases, more than half of the hemoglobin in the intestinal tract can be converted to porphyrins by intestinal bacteria.

The extraction procedure of the present invention preferably involves three extraction steps. The first involves an extraction of the porphyrins whose fluorescence assay is desired, as well as various other materials such as naturally occurring porphyrins and chlorophyll, leaving behind the iron salts, pigments and various other non-specific fluorescing material. While there may be several different ways to accomplish this initial extraction step, the preferred method of the present invention contemplates extracting the porphyrins into a mixture of ethyl acetate and acetic acid.

Following the removal of the iron salts and various non-specific fluorescing materials in the above step, the naturally occurring porphyrins such as coproporphyrin are separated and removed. In the preferred method of the present invention this is accomplished by first adding butyl alcohol to the ethyl acetate:acetic acid phase and then shaking with an alkaline mixture of potassium hydroxide and potassium acetate. The naturally occurring porphyrins as well as certain other materials exhibiting contaminating fluorescence are extracted into this alkaline mixture, thus permitting its removal from the ethyl acetate:butyl alcohol phase which contains the porphyrins derived from hemoglobin.

Thirdly, those porphyrins which are derived from hemoglobin (and related heme compounds) are extracted from chlorophyll, a major fluorescing fecal contaminant. In the preferred method, the porphyrins derived from hemoglobin are extracted into phosphoric acid leaving the chlorophyll behind in the ethyl acetate:butyl alcohol phase. In tests conducted on fecal samples utilizing the above extraction procedure, approximately 90% to 99% of the fluorescence assayed has been found to be due to protoporphyrin and other porphyrin derivatives of heme compounds.

Accordingly, it is an object of the present invention to provide an improved method of quantitatively determining the level of hemoglobin in a biological sample.

Another object of the present invention is to provide a method of isolating the porphyrins derived from hemoglobin and related heme compounds in a quantitative hemoglobin test based upon a fluorescence assay of the converted porphyrins.

A further object of the present invention is to provide a procedure for isolating the porphyrins derived from hemoglobin and related heme compounds in a quantitative hemoglobin test involving a fluorescence assay of the converted porphyrins in which the major fluorescence contaminants including naturally occurring porphyrins and chlorophyll, are separated from the porphyrins derived from hemoglobin.

Another object of the present invention is to provide an improved quantitative test for hemoglobin in feces in which information can be obtained to determine the relative location of bleeding in the gastrointestinal tract.

These and other objects of the present invention will become apparent with reference to the drawing, the description of the preferred method and the appended claims.

DESCRIPTION OF THE DRAWING

The only figure of the drawing illustrates a schematic representation of the extraction procedure of the present invention.

DESCRIPTION OF THE PREFERRED METHOD

The preferred method of the present invention has particular applicability to a quantitative test for hemoglobin in a biological sample in which the hemoglobin in such sample is converted to porphyrin followed by a determination of the level of such porphyrin.

In the preferred method, a sample of the biological material for which the quantitative hemoglobin level is desired is collected and combined with a reagent to convert the heme portion of the hemoglobin to porphyrin. While it is contemplated that the method of the present invention can be used in connection with many different kinds of biological samples, it has particular applicability to a biological sample such as feces, urine or gastric juice. The actual procedure for collecting a sample of the biological material can be any one of several procedures known in the art.

Following collection of the sample, the sample is combined with a reagent to convert the heme portion of the hemoglobin to porphyrin. One means for accomplishing this conversion is described in my copending patent application Ser. No. 190,399, filed Sept. 24, 1980, U.S. Pat. No. 4,378,971 in which the sample is combined with a reagent comprising a reducing acid and a reducing salt. More specifically, the preferred reagent to accomplish this conversion is comprised of a mixture of a reducing acid such as 2.0 or 2.5 molar oxalic acid and a 1.5 to 2.5% solution of a reducing salt such as ferrous oxalate or ferrous sulfate. By combining an effective quantity of this reagent with the test sample, the heme portion of the hemoglobin in the sample is converted to porphyrin. While some conversion will occur even at room temperature, the speed and efficiency of the conversion is increased at elevated temperatures. In the preferred method, the sample is heated for 20 minutes at a temperature of about 100° C. It is contemplated that various other means could be used to accomplish this conversion. When the conversion is complete, one can obtain quantitative information about the level of hemoglobin represented in the original test sample by determining the level of total converted porphyrins converted from hemoglobin. This is comprised of porphyrins converted from hemoglobin by intestinal bacteria as well as by the above described oxalic acid:ferous sulfate system.

At this stage in the procedure, however, there are normally several contaminants in the converted test sample which will affect the ability to accurately determine the level of porphyrin derived from hemoglobin, particularly when the level of porphyrin is determined by a fluorescence assay. Thus, the present invention also contemplates a procedure for isolating or separating out that portion of the porphyrin derived from hemoglobin so as to eliminate interfering components such as naturally occurring porphyrins, chlorophyll and various other materials having a fluorescence wavelength which coincides with the wavelength of converted porphyrin and thus affects the accuracy of the quantitative hemoglobin determination.

This procedure for isolating and separating the porphyrins derived solely from the conversion of the heme portion of hemoglobin, whether by bacteria or by selected chemicals or other means involves three general extraction steps. The first of these steps illustrated as step A in the drawing involves shaking a quantity of the test sample with a solvent which is capable of extracting those porphyrins whose ultimate determination is desired, namely, the porphyrins derived from hemoglobin. This solvent should also have properties which leave behind as many of the various other contaminants in the system as possible, particularly iron. In the preferred method illustrated as step A in the drawing, this solvent is an organic solvent such as ethyl acetate (EtOAc) containing a small amount of glacial acetic acid (HOAc). The purpose of the acetic acid is to insure extraction of the converted porphyrins and to insure solubility of the iron salt (iron acetate) and its removal in the aqueous phase. During the procedure, a portion of the test sample with the converted porphyrin is added to the ethyl acetate:acetic acid solution. After the combination is shaken and allowed to settle, porphyrins in the test sample, both naturally occurring porphyrins as well as converted porphyrins and chlorophyll, will be extracted into the ethyl acetate:acetic acid phase of the mixture and the iron, various pigments, medicines and other materials will remain behind in the aqueous phase. During this initial extraction step, potassium acetate is also added to improve the extraction performance. The primary purpose of the potassium acetate (KOAc) is to convert much of the oxalic acid to potassium oxalate, and thus reduce the acidity of the mixture to avoid losing some of the porphyrin into the aqueous phase. In the preferred method, one part by volume of the test sample with converted porphyrin is combined with six parts by volume of ethyl acetate:acetic acid solvent (comprising 20 parts by volume ethyl acetate to one part by volume of acetic acid) and two parts by volume of three molar potassium acetate.

It is contemplated that various solvent systems other than ethyl acetate and acetic acid could be utilized in this initial extraction step provided they perform the desired functions of extracting at least all of the porphyrins derived from the hemoglobin, but leaving behind or failing to extract various other contaminants, particularly iron. Other solvent systems such as ethylene dichloride, chloroform, perchloroethylene, carbon tetrachloride, tributyl phosphate, cyclohexanone, acetic acid, benzene, ether, toluene and amyl alcohol have been tried either alone or in combination, and all extract porphyrins to varying degrees, however, the ethyl acetate:acetic acid system is preferred. It is also contemplated that a material other than potassium acetate could be used to help maintain stability of the system and to reduce the acidity to avoid losing some of the porphyrin; however, this should preferably be a material which avoids the formation of a precipitate in the aqueous phase. Sodium salts such as sodium acetate, for example, yield insoluble sodium oxalate when used in the preferred method. Potassium oxalate, however, remains soluble under these conditions. Citrate, phosphate and other salts of potassium (or ammonium ion) were also tested, but the potassium acetate is the preferred salt.

Following this initial extraction step, a second extraction step is performed. In the second step illustrated as step B in the drawing, a portion of this ethyl acetate phase from step A is first added to butyl alcohol (BuOH). An aqueous solvent is then added to this mixture which extracts numerous impurities, including the naturally occurring porphyrins such as coproporphyrin, from the ethyl acetate:butyl alcohol phase, but which leaves the porphyrin derived from hemoglobin behind. To accomplish this, it is preferable for this aqueous solvent to be strongly alkaline and to have a relatively high concentration of soluble salt. In the preferred method, a portion of the ethyl acetate phase from step A is combined with a mixture of potassium hydroxide and potassium acetate to achieve better alkalinity and a high concentration of the potassium salt. More particularly, the preferred method contemplates combining one part by volume of the ethyl acetate phase from step A with 0.4 parts by volume of butyl alcohol and three parts by volume of a mixture of one molar potassium hydroxide containing three molar potassium acetate. It has been found that this reagent is effective to extract virtually all of the contaminating naturally occurring porphyrins and additional impurities from the ethyl acetate:butyl alcohol phase. The butyl alcohol is added to improve the performance of this particular extraction step B. Its purpose is to increase the ethyl acetate solubility of porphyrins which are derived from hemoglobin and prevent their loss into the aqueous phase. Although butyl alcohol, potassium hydroxide and potassium acetate are the preferred components of this second extraction step, it is contemplated that other components could be substituted provided they accomplish the desired purpose of step B which is to extract only porphyrins which are not derived from hemoglobin and other impurities from the ethyl acetate phase.

At this point in the method of the present invention, after the reagents in step B have been mixed and allowed to settle, the sample comprises an aqueous phase which includes the porphyrins not derived from hemoglobin and also an ethyl acetate:butyl alcohol phase which includes chlorophyll and porphyrins derived from hemoglobin. A third extraction step is then performed. As illustrated by step C in the drawing, this third extraction step involves combining a portion of the ethyl acetate:butyl alcohol phase from step B with a solvent effective to extract the porphyrins derived from hemoglobin while leaving behind chlorophyll, a major fluorescing fecal contaminant. In the preferred method, this solvent is a combination of two molar phosphoric acid and acetic acid is approximately a 9:1 ratio. It is contemplated that other strong acids such as hydrochloric acid can also be used in place of the phosphoric acid:acetic acid solvent, although the latter is preferred.

The preferred method contemplates adding one part by volume of the ethyl acetate:butyl phase from step B with three parts by volume of the phosphoric acid:acetic acid component. While various other concentrations may be satisfactory, the above is preferred. It should be noted that the amount of butyl alcohol added in step B and which remains in the ethyl acetate:butyl alcohol phase in step C is important to some extent in the performance of the third extraction step. Specifically, the addition of too much butyl alcohol in step B will result in some of the porphyrin derived from hemoglobin staying in the ethyl acetate:butyl alcohol phase of step C. Thus, the amount of butyl alcohol added in step B should be lower than the amount which would cause this result. At the same time, however, enough butyl alcohol must be added in step B to keep the porphyrin derived from hemoglobin in that step in the ethyl acetate:butyl alcohol phase.

At this point in the procedure, the bottom phosphoric acid:acetic acid aqueous phase includes the porphyrins converted from hemoglobin while the top ethyl acetate:butyl alcohol phase contains the chlorophyll and other contaminants including fat-soluble compounds. A sample of this phosphoric acid:acetic acid aqueous phase containing the porphyrins derived from hemoglobin can then be assayed to determine the level of porphyrin and thus of the level of hemoglobin in the original test samples. While it is contemplated that various means could be used to determine the level of porphyrin in this converted sample, the preferred method contemplates a fluorescence assay. By comparing the fluorescence of the porphyrins and the converted sample to the fluorescence level of a standard prepared from known concentrations of hemoglobin, information with regard to the level of hemoglobin in the test sample can be calculated. In fecal samples tested to date, it has been found that over 90% of the fluorescence assayed in this final extract is due to porphyrins derived from heme compounds.

By performing the above extraction procedure improved results can be obtained in a quantitative test for hemoglobin in which the hemoglobin in the test sample is first converted to porphyrin followed by a determination of the level of such porphyrin. The extraction steps are particularly applicable if the level of converted porphyrin is determined by a fluorescence assay. Utilization of this procedure will result in accurate quantitative determination of the amount of hemoglobin in the test sample.

A further aspect of the present method is that it also allows additional meaningful information to be obtained with respect to the location of bleeding if the biological sample is feces. This is accomplished by duplicating the procedure described above, both with respect to the preparation of the test sample, etc. as well as the extraction procedure, except that a solution of citric acid or some other non-reducing system is used in place of the reducing acid:reducing salt reagent. Because citric acid is not a reducing acid and thus does not perform the reducing function of converting the heme portion of the hemoglobin to porphyrin, no significant externally stimulated conversion of hemoglobin to porphyrin occurs. Thus, the only porphyrins derived from hemoglobin which exist in this test sample prior to (and after) application of the extraction steps is protoporphyrin and other porphyrins which have been converted from hemoglobin via naturally occurring intestinal bacteria. Following the performance of the above-described extraction steps on the test sample which has been combined with citric acid, a determination of the level of porphyrin is made such as via a fluorescence assay. This data is then used to calculate the amount of hemoglobin in the initial test sample which had been converted to porphyrin by naturally occurring bacteria. This amount, of course, would be lower than the amount calculated using the reducing acid:reducing salt reagent since the procedure conducted with this latter reagent includes porphyrins which are present in the citric acid as a result of bacterial conversion as well as those derived from additional hemoglobin being converted to porphyrin as a result of the reducing acid:reducing salt reagent. By comparing the relative hemoglobin amounts determined in these two samples, valuable information can be obtained with regard to the location of bleeding. For example, if the value of the citric acid simple is less than 5 or 10% that of the oxalic acid:ferous sulfate sample, this would indicate that the bleeding is occurring at a relatively low point in the gastrointestinal tract since there would be less time for naturally occurring substances such as intestinal bacteria to convert hemoglobin to porphyrins. It could also mean that the intestinal bacteria have been destroyed by appropriate antibiotic drugs. On the other hand, if this percentage is about 30% or more, this would indicate that the bleeding site is probably higher in the intestinal tract. That, the naturally occurring intestinal bacteria would have a greater time to convert hemoglobin to porphyrin.

Although the description of the preferred method of the present invention has been quite specific, it is contemplated that various changes could be made without deviating from the spirit of the present invention. Accordingly, it is contemplated that the scope of the present invention is dictated by the appended claims rather than by the description of the preferred method.

I claim:

1. A method of quantitatively determining the amount of hemoglobin in a biological material comprising the steps of:
    preparing a test sample of said biological material;
    converting the hemoglobin in said test sample to hemoglobin derived porphyrins;
    performing an extraction procedure for the purpose of separating the hemoglobin derived porphyrins from various contaminants in said test sample including mixing said test sample with a first extraction reagent comprising an organic solvent effective to separate the hemoglobin derived porphyrins from iron;
    allowing said test sample and first extraction reagent mixture to separate into an aqueous phase containing iron and a supernatant containing hemoglobin-derived porphyrins;
    mixing said supernatant with a second extraction reagent comprising an alkaline solvent containing a soluble salt effective to separate the hemoglobin derived porphyrins from naturally occurring porphyrins;
    allowing said supernatant and second extraction reagent mixture to separate into a phase containing naturally occurring porphyrins and a second supernatant containing hemoglobin derived porphyrins; and
    determining the amount of hemoglobin derived porphyrins.

2. The method of claim 1 wherein said organic solvent is selected from the group consisting of: ethyl acetate, butyl alcohol, amyl alcohol, chloroform, perchlorethylene, carbon tetrachloride, cyclohexanone, tributyl phosphate, toluene, acetic acid, and ethylene chloride.

3. The method of claim 1 wherein said first extraction reagent includes an ethyl acetate:acetic acid mixture.

4. The method of claim 1 wherein said second extraction reagent includes potassium hydroxide.

5. The method of claim 1 wherein said second extraction reagent includes potassium hydroxide and potassium acetate.

6. The method of claim 1 wherein said second extraction reagent includes butyl alcohol.

7. The method of claim 1 wherein said biological material is feces, urine or gastric juice.

8. The method of claim 1 including determining the level of hemoglobin derived porphyrin via a fluorescence assay.

9. The method of claim 1 wherein said first extraction reagent includes an effective quantity of a suitable salt to decrease acidity.

10. The method of claim 9 wherein said suitable salt is potassium acetate.

11. The method of claim 1 wherein said extraction further includes mixing said second supernatant with a third extraction reagent comprising a strong acid effective to separate the hemoglobin derived porphyrins.

12. The mixture of claim 11 wherein said strong acid comprises a mixture of phosphoric acid and acetic acid.

13. A method of quantitatively determining the amount of hemoglobin in a biological material comprising the steps of:

preparing a test sample of said biological material;

converting the hemoglobin in said test sample to hemoglobin derived porphyrins;

performing an extraction procedure for the purpose of separating the hemoglobin derived porphyrins from various contaminants in said test sample including combining said test sample with an extraction reagent comprising an alkaline solvent containing a soluble salt effective to separate the hemoglobin derived porphyrins from naturally occurring porphyrins; and determining the level of hemoglobin derived porphyrins.

14. The method of claim 13 wherein said extraction procedure for separating hemoglobin derived porphyrins from naturally occurring porphyrins includes combining of quantity of butyl alcohol with said test sample.

15. The method of claim 13 wherein said alkaline solvent includes potassium hydroxide.

16. The method of claim 15 wherein said soluble salt includes potassium acetate.

17. A method of analyzing a test sample of feces to determine information regarding the total amount of hemoglobin originally in said test sample and the location of the source of such hemoglobin in the gastrointestinal tract, in which said test sample is expected to contain currently existing hemoglobin and porphyrins derived from the conversion of previously existing hemoglobin as a result of exposure to various naturally occurring converting substances in the gastrointestinal tract, said method comprising the steps of:

preparing a test sample of feces;

converting substantially all of the currently existing hemoglobin in said test sample to hemoglobin derived porphyrins by combining said test sample with a converting reagent;

determining the total amount of hemoglobin derived porphyrins in said test sample resulting from combining said test sample with said converting reagent and its exposure to naturally occurring converting substances in the gastrointestinal tract;

preparing a duplicate test sample of feces;

determining the amount of hemoglobin derived porphyrins in said duplicate test sample resulting from exposure to naturally occurring substances in the gastrointestinal tract; and determining the source of the hemoglobin in the test sample by comparing the total amount of hemoglobin derived porphyrins in said test sample with the amount of hemoglobin derived porphyrins in said duplicate test sample resulting from exposure to naturally occurring substances in the gastrointestinal tract.

18. The method of claim 17 wherein the step of determining information regarding the amount of hemoglobin includes combining said duplicate test sample with a blank reagent which does not convert significant amounts of hemoglobin to porphyrin.

19. The method of claim 18 wherein said blank reagent is comprised of citric acid.

20. The method of claim 17 wherein the step of determining information regarding the amount of hemoglobin includes separating the total amount of hemoglobin derived porphyrins from naturally occurring porphyrins in said test sample and separating the hemoglobin derived porphyrins from naturally occurring porphyrins in said duplicate test sample.

21. The method of claim 20 wherein the step of separating the hemoglobin derived porphyrins from the naturally occurring porphyrins in each of said test sample and said duplicate test sample includes mixing said test sample and said duplicate test sample, respectively, with an extraction reagent comprising an alkaline solvent containing a soluble salt.

22. The method of claim 21 wherein said extraction reagent includes potassium hydroxide.

* * * * *

UNITED STATES PATENT AND TRADEMARK OFFICE
CERTIFICATE OF CORRECTION

PATENT NO. : 4,567,148

DATED : January 28, 1986

INVENTOR(S) : Samuel Schwartz

It is certified that error appears in the above-identified patent and that said Letters Patent is hereby corrected as shown below:

```
In column 1, line 22, delete the word "and" (2nd occurrence)
and insert --are--.

In column 8, line 64, delete the word "mixture"
and insert --method--.
```

Signed and Sealed this

Twenty-seventh Day of May 1986

[SEAL]

Attest:

Attesting Officer

DONALD J. QUIGG

Commissioner of Patents and Trademarks

UNITED STATES PATENT AND TRADEMARK OFFICE
CERTIFICATE OF CORRECTION

PATENT NO. : 4,567,148
DATED : January 28, 1986
INVENTOR(S) : Samuel Schwartz

It is certified that error appears in the above-indentified patent and that said Letters Patent is hereby corrected as shown below:

In col. 1, line 7, before the "BACKGROUND OF THE INVENTION" heading and after the sentence ending with "U.S. Pat. No. 4,378,971", please add the following:

> "This invention was made with government support under R01-AM 12466 and GM 14086 awarded by the National Institutes of Health. The government has certain rights in the invention."

Signed and Sealed this

First Day of November, 1994

Attest:

BRUCE LEHMAN

Attesting Officer

Commissioner of Patents and Trademarks